United States Patent [19]

Primbsch

[11] 4,180,324
[45] Dec. 25, 1979

[54] METHOD AND APPARATUS FOR MEASURING DEFORMATION OF A WORKPIECE SURFACE RESPONSIVE TO ULTRASONIC ENERGY

[75] Inventor: Erik Primbsch, Cologne, Fed. Rep. of Germany

[73] Assignee: Krautkramer-Branson, Inc., Stratford, Conn.

[21] Appl. No.: 839,168

[22] Filed: Oct. 4, 1977

[30] Foreign Application Priority Data

Mar. 5, 1977 [DE] Fed. Rep. of Germany ....... 2709686

[51] Int. Cl.² .............................................. G01B 9/02
[52] U.S. Cl. ..................... 356/35.5; 73/657; 356/360
[58] Field of Search .................... 356/106 R, 109, 360, 356/35.5; 73/657

[56] References Cited

U.S. PATENT DOCUMENTS

| | | | |
|---|---|---|---|
| 3,319,515 | 5/1967 | Flournoy | 356/108 |
| 3,503,012 | 3/1970 | Gillard | 356/106 R X |
| 3,535,024 | 10/1970 | Schindler | 356/106 R X |
| 3,633,987 | 1/1972 | Brooks | 356/109 X |
| 3,822,942 | 7/1974 | Hock | 356/106 R |
| 4,046,477 | 9/1977 | Kaule | 356/109 |

OTHER PUBLICATIONS

Born et al., *Principles of Optics*, Pergamon Press, pp. 315-322, 1959.

*Primary Examiner*—John K. Corbin
*Assistant Examiner*—Matthew W. Koren
*Attorney, Agent, or Firm*—Ervin B. Steinberg; Philip J. Feig

[57] ABSTRACT

This invention relates to an interferometric laser method and apparatus for sensing the acoustic wave responsive deformation of a workpiece surface. A laser provides a coherent beam of light which after reflection at the workpiece surface is split into a first measuring beam portion and a second reference beam portion, the latter portion being delayed by being transmitted over a long delay path. The optical length of the delay path is dimensioned to be a multiple integer of the optical length of the resonator of the laser.

2 Claims, 1 Drawing Figure

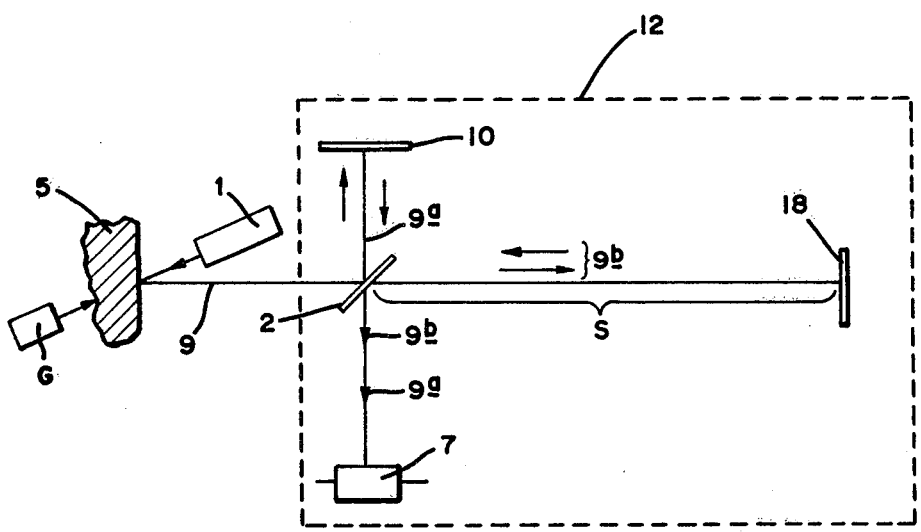

METHOD AND APPARATUS FOR MEASURING DEFORMATION OF A WORKPIECE SURFACE RESPONSIVE TO ULTRASONIC ENERGY

FIELD OF THE INVENTION

This invention relates to an optical interferometric method and aparatus for measuring the deformation of a workpiece surface whereby such deformation is caused by ultrasonic energy introduced into the workpiece. More particularly, this method and apparatus concern an arrangement for sensing ultrasonic energy free of physical contact with a heated workpiece or one which translates at a high speed relative to a test station, for instance, plate stock. The present invention is related to U.S. Pat. No. 4,046,477 in the name of W. Kaule, dated Sept. 6, 1977, entitled "Interferometric Method and Apparatus For Sensing Surface Deformation of a Workpiece Subjected to Acoustic Energy".

BRIEF SUMMARY OF THE INVENTION

In accordance with the disclosure of W. Kaule supra, the workpiece surface is illuminated with a beam of monochromatic coherent laser energy. The reflected light from the workpiece surface is split at a beam splitter and one beam portion is transmitted to light receiving means as a measuring beam, whereas the other beam portion reaches the light receiving means after passing over a delay path and after combining with the measuring beam portion at the receiving means forms the main beam.

Using the measurement method described in the Kaule patent supra, it is necessary that the laser resonate only in one mode in order that the long delay path accomodating the ultrasonic frequency is not subjected to other conditions. The resonator of a laser is driven with harmonics of very high order, i.e. multimode laser. For instance, in the case of a resonator of 500 mm length and a light wavelength of 500 nanometers the ordinal number of harmonics has a magnitude in the order of $10^6$. A fundamental characteristic of a laser resides in the fact that generally those harmonics can exist which fall within the linewidth of the laser operation.

A typical commercially available argon-ion laser for a given operating condition has an emission line at 500 nm and a line width in the order of 5 GHz. For the frequency separation $\Delta f$ of the modes the relation $$\Delta f = c/2L$$

applies, wherein c denotes the speed of the light in the resonator material and L the length of the resonator. In the given example:

$$\Delta f = 3 \times 10^8 \text{ Hz} = 0.3 \text{ GHz}$$

For the argon-ion laser, based on the above line width, a maximum of sixteen modes can be excited. Practice has proven that not all of the modes possible will be present. When interference with a beam portion is provided and such portion is transmitted over a very long delay path, as necessary for the present invention, it can not be assured that thereafter phase coincidence, as is required by the coherent wave condition, still exists for all of the modes. Using delays of such a large magnitude for a beam portion not all modes interfere in the same trend and the resultant interference contrast is significantly lower. Interference contrast K is the ratio of the difference between the maximum ($I_{max}$) and minimum ($I_{min}$) light intensity to the maximum light intensity. Hence:

$$K = (I_{max} - I_{min})/I_{max}.$$

The reduction of interference contrast causes a loss of sensitivity during measurements since the interference contrast determines the steepness of the interferometer operating curve, that is, the dependence of the brightness upon the phase change. Phase changes occur as the result of ultrasonic wave induced deformations of the workpiece surface and cause, in the event of high interference contrast, large changes in brightness, and in the event of a low interference contrast correspondingly small brightness changes.

When many modes exist which no longer interfere in-phase, the brightness change (sensitivity) $I_{max} - I_{min}$ becomes smaller, assuming given changes of ultrasonic wave intensity, since $I_{min}$ becomes larger and $I_{max}$ smaller. Therefore, it will be necessary to operate the resonator of the laser in such a manner that only one mode is present. This condition represents a loss of intensity of fifty percent or more of the total available light intensity.

An object of this invention is to overcome the disadvantage stated above and to utilize a laser at its optimum condition. More specifically, it is desired to use a laser which within its operational limits operates with all modes and to use these modes for deriving maximum output power and, hence, maximum light intensity after interference and provide simultaneously high interference contrast.

In accordance with the present invention the above described object is achieved by dimensioning the optical length of the delay path, which serves for delaying the laser beam portion used as a reference beam and which is made to accomodate the period of the sound wave, to be a multiple integer of the laser resonator optical length.

The advantage of dimensioning the delay path length in relation to the resonator length of the laser will be more clearly apparent from the following description when taken in conjunction with the accompanying drawing:

BRIEF DESCRIPTION OF THE DRAWING

The single FIGURE is a schematic line diagram for explaining the present invention.

DETAILED DESCRIPTION OF THE INVENTION

When operating a multimode laser, standing waves are present in the resonator. All modes are of the same phase at the resonator reflectors. This spatial phase condition between the modes, determined by the geometry of the resonator, is retained in the light wave transmitted to the outside. If in an interferometer, according to Michelson, two beam portions which are split from a common light source are brought to interference, all resulting modes exhibit the same brightness, providing the path difference between the two beam portions is zero or both paths differ by only a few light wavelengths. This condition exists since the relative frequency deviation of the modes among themselves is small.

The interference contrast, in the above stated case, is nearly unity. If the difference in optical path length between the beam portions of the interferometer is increased by a few centimeters, the phase difference between individual modes is increased to such an extent that some modes at interference provide, for instance, brightness whereas other modes for the same mechanical path length difference provide darkness. Thus, the interference contrast is worsened. However, when the effective optical distance between the interferometer reflectors equals the resonator length, all modes are superposed with the same phase. The interference contrast again aproaches unity. This phenomenon repeats itself after one resonator length if one interferometer reflector is moved. When the distance between the interferometer reflectors becomes a multiple integer of the length of the laser resonator, whose light is used for illumination, the interference contrast always assumes the maximum value of nearly unity. Referring to the FIGURE which shows the arrangement disclosed in the patent to Kaule supra, the interferometer is denoted by numeral 12. A multimode laser G provides pulsed light energy to a workpiece 5 to cause an acoustic wave in the workpiece. The resultant surface deformation is sensed by using a second laser 1 which directs a coherent light beam upon the workpiece surface. A reflected light beam 9 is transmitted to a beam splitter 2 which causes a first beam portion 9a to be directed toward mirror 10 which reflects such portion. The reflected beam then passes through beam splitter 2 and is transmitted as beam portion 9a for incidence upon a photoelectric sensing means 7. The other beam portion 9b, split at the beam splitter 2, is transmitted over a delay path S toward the mirror 18, reflected thereat and transmitted back toward the splitter 2 from where the beam portion 9b, now delayed in time, is transmitted for interference to the photoelectric sensing means 7. The length of the optical delay path traversed by the beam portion is 2S. The mirror 18 provides a folded light path as is well known in optics.

It will be apparent that the difference between both light paths amounts to several powers of ten of the wavelength of light. In accordance with the invention disclosed heretofore, the delay path length between the reflecting surfaces 2 and 18 of the interferometer, distance S, equals a multiple integer of the resonator length of the laser providing the light beam.

If S is the length of the delay path, n is a positive integer and R denotes the resonator length of the laser, the requirement $$S = n \times R$$

is derived. In this equation n is to be selected so that the condition for the required transit time, i.e. meeting the requirement of the acoustic wave frequency, is met optimally, the half period of the acoustic wave being equal to the delay time. Meeting this condition presents no particular problem in the ultrasonic nondestructive testing art since for the ultrasonic wave frequencies in the range of a few Megahertz, delay periods of 50 to 100 nanoseconds are required, whereas the resonator length present in conventional available lasers corresponds to a transit time of one to three nanoseconds.

When dimensioning the delay path length as a function of the resonator length, all of the available modes of the laser can be used advantageously for the interferometric measurement of surface deformations as is desirable for the ultrasonic nondestructive testing of workpieces.

What is claimed is:

1. The method of sensing by optical interference the deformation of a workpiece surface resulting from acoustic energy in the workpiece comprising:
    applying wave energy to a workpiece for causing surface deformation of such workpiece;
    transmitting a coherent beam of light from a multimode laser upon the surface of the workpiece for sensing such deformation;
    splitting said beam after reflection at said workpiece surface into a measuring beam portion and a reference beam portion;
    transmitting said measuring beam portion to photoelectric sensing means, and
    transmitting said reference beam portion over a delay path and thereafter bringing said reference beam to coincidence with said measuring beam portion at said photoelectric means, said delay path being dimensioned to cause its optical length to be a multiple integer of the optical length of the resonator of said laser.

2. An apparatus for sensing by optical interference the deformation of a workpiece surface resulting from acoustic energy in such workpiece comprising in combination:
    means coupled for applying wave energy to a workpiece for causing surface deformation of such workpiece;
    a multimode laser disposed for directing its beam upon a surface portion of the workpiece for sensing such deformation;
    an optical beam splitter;
    an optical delay path and photoelectric sensing means so disposed that said laser beam responsive to being directed upon the surface portion of the workpiece and being reflected thereat reaches said beam splitter and a first measuring beam portion leaving said splitter is incident upon said sensing means, while a second beam portion leaving said splitter as a reference beam is transmitted over said delay path toward said sensing means for coincidence with said first beam portion, and
    said delay path being dimensioned to cause its optical length to be a multiple integer of the optical length of the resonator of said laser.

* * * * *